(12) United States Patent
Sunenshine et al.

(10) Patent No.: US 12,311,093 B2
(45) Date of Patent: May 27, 2025

(54) MANUAL CLOT ASPIRATION AND FILTRATION SYSTEM AND METHOD OF REMOVING A CLOT

(71) Applicant: First Pass, LLC, Paradise Valley, AZ (US)

(72) Inventors: Peter J. Sunenshine, Paradise Valley, AZ (US); Kevin Hirsch, Phoenix, AZ (US); Joseph Barrett, Tempe, AZ (US)

(73) Assignee: First Pass, LLC, Paradise Valley, AZ (US)

(*) Notice: Subject to any disclaimer, the term of this patent is extended or adjusted under 35 U.S.C. 154(b) by 604 days.

(21) Appl. No.: 17/687,912

(22) Filed: Mar. 7, 2022

(65) Prior Publication Data

US 2022/0226555 A1 Jul. 21, 2022

Related U.S. Application Data

(63) Continuation-in-part of application No. 16/960,847, filed as application No. PCT/US2020/019081 on Feb. 20, 2020, now Pat. No. 11,266,825.

(51) Int. Cl.
*A61M 1/36* (2006.01)

(52) U.S. Cl.
CPC .......... *A61M 1/3659* (2014.02); *A61M 1/367* (2013.01)

(58) Field of Classification Search
None
See application file for complete search history.

(56) References Cited

U.S. PATENT DOCUMENTS

| | | |
|---|---|---|
| 4,006,745 A | 2/1977 | Sorenson et al. |
| 4,954,251 A | 9/1990 | Barnes et al. |
| 5,055,198 A | 10/1991 | Shettigar |
| 5,076,933 A | 12/1991 | Glenn et al. |
| 5,279,550 A | 1/1994 | Habib et al. |
| 5,951,870 A | 9/1999 | Utterberg |
| 6,059,745 A | 5/2000 | Gelbfish |
| 6,558,341 B1 | 5/2003 | Swisher |
| 7,332,096 B2 | 2/2008 | Blickhan |
| 7,540,958 B2 | 6/2009 | Chevallet et al. |
| 7,527,377 B2 | 8/2009 | Herbst |
| 8,100,849 B2 | 1/2012 | Movahed |
| 8,153,008 B2 | 4/2012 | Nilsson |
| 8,206,594 B2 | 6/2012 | Yoganathan et al. |
| 8,366,649 B2 | 2/2013 | Ibragimov |

(Continued)

*Primary Examiner* — Jonathan M Peo
(74) *Attorney, Agent, or Firm* — Invention To Patent Services; Alex Hobson

(57) ABSTRACT

A manual clot aspiration and filtration system enables a method of removing a clot without general anesthesia and the expense of an operating room. An aspiration and filtration system for bodily fluid utilizes a syringe coupled with a filter unit to draw bodily fluid through the filter unit to collect debris on the filter. A flow valve may then be turned and the plunger depressed to force the filtered fluid back into the body. The filter may be configured to capture particles such as blood clots and plaque. The filter unit has a cover that can be removed for inspection and/or removal of the collected debris. When the cover is replaced, trapped air may be removed by turning the flow-valve to a purge direction and pressing the plunger into the syringe to force fluid back toward the filter unit to purge the trapped air through the purge valve.

20 Claims, 15 Drawing Sheets

(56) References Cited

U.S. PATENT DOCUMENTS

| | | | |
|---|---|---|---|
| 8,679,076 B2 | 3/2014 | Kurzweil et al. | |
| 9,839,716 B1 | 12/2017 | Nowakowski | |
| 10,328,193 B2 | 6/2019 | Frugier | |
| 2001/0049486 A1* | 12/2001 | Evans | A61M 1/3621 604/35 |
| 2004/0019310 A1 | 1/2004 | Hogendijk | |
| 2014/0364833 A1 | 12/2014 | Orr et al. | |
| 2018/0042623 A1* | 2/2018 | Batiste | A61M 25/0075 |
| 2020/0046368 A1* | 2/2020 | Merritt | A61M 1/815 |

* cited by examiner

MANUAL CLOT ASPIRATION AND FILTRATION SYSTEM AND METHOD OF REMOVING A CLOT

CROSS REFERENCE TO RELATED APPLICATIONS

This application is a continuation in part of U.S. patent application Ser. No. 16/960,847, filed on Jun. 8, 2020 and currently pending, which is a national stage application of PCT application No. PCT/US2020/019081, filed on Feb. 20, 2020 and currently pending; the entirety of both applications are hereby incorporated by reference herein.

BACKGROUND OF THE INVENTION

Field of the Invention

The invention relates a manual clot aspiration and filtration system and a method of removing a clot using said system.

Background

Clot removal is typically done via methods requiring the use of an operating room and in many cases requires the patient to be put under general anesthesia. This is expensive and introduces risk to the patient due to the general anesthesia.

SUMMARY OF THE INVENTION

The invention is directed to a manual clot aspiration and filtration system and a method of removing a clot using said system. The manual clot aspiration and filtration system of the present invention may be performed in a general exam or procedure room not requiring the expense of an operating room. In addition, this procedure may be done without general anesthesia, thereby reducing the risk to the patient and providing a much more cost-effective procedure.

An exemplary aspiration and filtration system for bodily fluid comprises a pump, such as a syringe couple with a filter unit to draw bodily fluid, such as blood, through the filter unit and filter configured therein, to collect debris, such as clot particles or plaque. A flow-valve may be turned to change the flow from the syringe and the syringe plunger may be depressed to force the filtered fluid back into the body. The filter may be configured to capture particles and debris in the bodily fluid such as debris from blood clots, plaque and the like. The filter unit is configured with a cover that enables the user to inspect and/or remove the debris from the filter. The filter may be changed out for a new filter in some cases. When the cover is replaced onto the filter unit, air will be trapped in the filter unit that must be removed before proceeding. Introducing air back into the patient could create a life-threatening condition depending on the type of bodily fluid filtered with the system. A purge valve is coupled to the filter housing and configured to allow air to be forced through the purge valve when the flow-valve is turned in a purge direction and the plunger is forced into the syringe barrel to force fluid back toward the filter unit. When the air is effectively purged, the flow-valve can be turned to a filter or return direction to continue the method. The flow-valve may be turned to a return direction to force bodily fluid from the syringe back into the patient or to discard the bodily fluid. In some cases, the bodily fluid may be returned to the patient and in some cases, it may be discarded. The method may be repeated any number of times until a desired amount of debris is removed, or until no more particles and debris are captured by the filter.

An exemplary aspiration and filtration system comprises an inlet sheath, such as a conduit, that is coupled between a patient and the filter unit. An inlet one-way valve may be configured between the patient and the filer unit, such as along the inlet sheath, to allow bodily fluid to flow from the patient into the filter unit but not back from the filter unit to the patient, as it may include debris. An exemplary aspiration and filtration system comprises a return sheath, such as a conduit, that is coupled between the syringe and the patient and is configured to carry bodily fluid from the syringe back to the patient. Note that the bodily fluid may also be expelled from the system.

An exemplary flow-valve is configured downstream of the filter unit and is coupled with the syringe, the return sheath and the filter unit. Pulling up on the plunger, when the flow valve is in a filter direction, that blocks flow to the return sheath, results in bodily fluid being drawn from the patient, through the filter unit and into the syringe. The plunger may be pulled manually out from the syringe to draw fluid from the patient. The flow-valve may be turned to a return direction, wherein flow to the filter unit is blocked, and the plunger may be forced back into the syringe barrel to force bodily fluid therein through the return sheath and back into the patient or to discard the bodily fluid. After drawing bodily fluid through the filter, the cover of the filter unit may be removed to inspect any debris collected by the filter. As described herein, the debris may be removed along with the filter and the filter may be replace before proceeding. The debris may be inspected, weighed or otherwise characterized and analyzed for the procedure. The detachably attachable cover may be placed back on the filter unit or filter housing. The cover may form an air-tight seal with the filter housing and a gasket may be configured between the cover and the filter housing. With the cover attached to the filter housing, air may be forced out of the filter unit and system by turning the flow-valve to a purge direction that blocks flow to the return sheath, and pushing the plunger back into the syringe barrel. The bodily fluid within the syringe will be forced back into the filter housing and the purge valve, configured atop the filter housing, will allow entrapped air to escape as the incompressible fluid displaces the trapped air.

An exemplary purge valve may be configured with an outlet opening that is above the top of the filter housing and may be coupled with the filter cover. This configuration with the outlet opening above the filter housing or above the enclosed space of the filter unit ensures that the air is displaced out of the filter housing before resuming the method. The enclosed space of the filter unit may extend from the inlet one-way valve to the outlet of the filter housing.

The method of manually removing clots or other debris from bodily fluid may be performed under less stringent regulations and may not require general anesthesia. The bodily fluid may be pulled through the filter unit and returned to the patient or discarded any number of times or cycles. After a desired amount of bodily fluid has passed through the filter unit, the cover of the filter housing may be removed to inspect how much debris was collected. A determination may then be made to continue with the filtration or terminate the procedure. In some cases, the debris may be removed for weighing or other analysis before resuming the method.

An exemplary filter may be configured to capture debris that is relatively small and may have a mean pore or opening size of no more than 100 microns, no more than 50 microns, no more than 25 microns, no more than 10 microns and any range between and including the mean filter pore sizes provided. The mean pore size of a filter material may be determined through capillary flow porometry and may be determine using a Porolux 500 or equivalent from POROMETER LLC, York, PA. Another filter may be a high-flow low priming microaggregate filter with a 40 micron screen from Terumo, Ann Arbor, MI. A filter may provide a filter efficiency of more than 99.9% collection of particles that are more than 100 microns, more than 50 microns, more than 25 microns, more than 10 microns. It is to be understood that the filter pore size and efficiency of filtration required may change depending on the type of bodily fluid filtered and the procedure.

An exemplary filter housing and filter configured therein may be a suitable size for the amount of debris to be collected and the volume of bodily fluid withdrawn by the syringe. The filter may be rectangular and may be about 50 mm by 50 mm, or 2500 mm$^2$, about 35 mm by 35 mm or 1225 mm$^2$, or about 25 mm by about 25 mm or 625 mm$^2$ and any size or area between the values provided. The filter housing may hold a volume of about 150 cc or less, or about 100 cc or less, or about 75 cc or less, or about 50 cc or less and any volume between and including the volumes provided. The filter housing may be about the same or a smaller in volume than the volume of the syringe. It is important to be able to fully fill the filter housing with the bodily fluid from the syringe.

The syringe, or syringe barrel may have a volume that is large enough to draw an effective amount of fluid from the patient, such as about 200 cc or more, about 150 cc or more, about 100 cc or more, about 50 cc or more and any range between and including the volumes provided. The volume of the syringe may be larger than the volume of the filter housing to enable any and all trapped air to be forces out of the filter housing when the bodily fluid is forced back into the filter housing during an air purge step of the method. The filter housing volume may be at least 10% less than the volume of the syringe, or at least 20% less than the volume of the syringe.

A pump, as used herein, is a device that may be used force bodily, such as blood, from the patient into the filter unit and subsequently force said bodily fluid back to the patient through the return sheath. A pump, which may be a syringe or other manual pumping implement, or a powered pump, such as an electrically powered including, but not limited to, peristaltic pump, displacement pump, diaphragm pump, piston pump, centrifugal pump, a vacuum pump and the like. The pump may be configured between the filter unit and the return sheath, between the inlet sheath and the filter unit, or may be coupled with the filter unit, such as being coupled with the filter housing for example. The pump may force bodily fluid into filter unit or may draw bodily fluid from the filter unit.

The manual clot aspiration and filtration system may be used for thrombectomy and filtration of endovascular debris/thrombus. The cover of the filter unit may be removed to inspect the thrombus and debris, including weighing the collected material and comparing the general amount by weight or volume to that predicted through fluoroscopy.

The summary of the invention is provided as a general introduction to some of the embodiments of the invention, and is not intended to be limiting. Additional example embodiments including variations and alternative configurations of the invention are provided herein.

BRIEF DESCRIPTION OF SEVERAL VIEWS OF THE DRAWINGS

The accompanying drawings are included to provide a further understanding of the invention and are incorporated in and constitute a part of this specification, illustrate embodiments of the invention, and together with the description serve to explain the principles of the invention.

Figure 1:
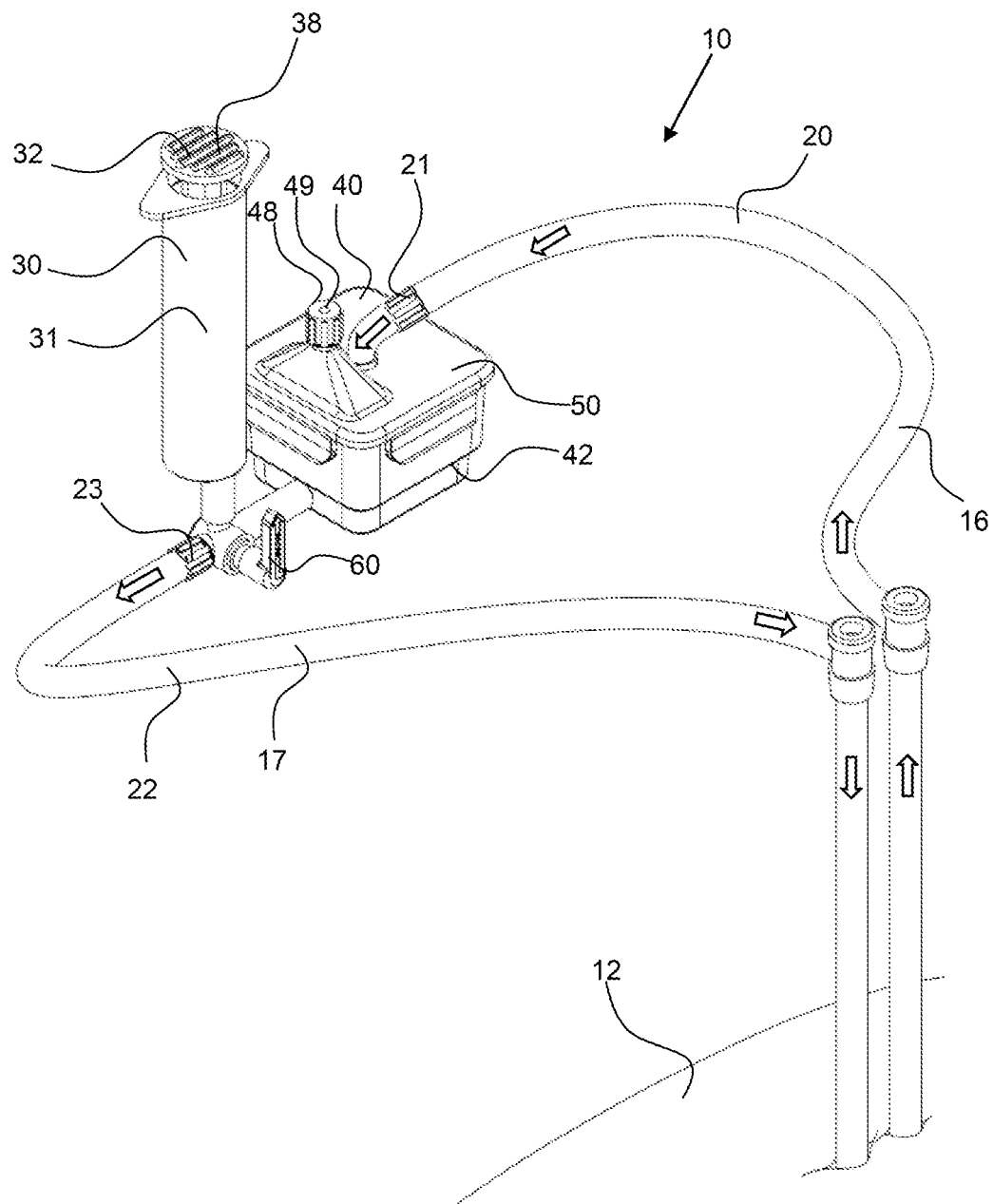
FIG. 1 shows a perspective view of an exemplary aspiration and filtration system with the inlet-sheath and return-sheath being coupled with the vascular system of a patient.

Corresponding reference characters indicate corresponding parts throughout the several views of the figures. The figures represent an illustration of some of the embodiments of the present invention and are not to be construed as limiting the scope of the invention in any manner. Further, the figures are not necessarily to scale, some features may be exaggerated to show details of particular components. Therefore, specific structural and functional details disclosed herein are not to be interpreted as limiting, but merely as a representative basis for teaching one skilled in the art to variously employ the present invention.

DETAILED DESCRIPTION OF THE ILLUSTRATED EMBODIMENTS

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Certain exemplary embodiments of the present invention are described herein and are illustrated in the accompanying figures. The embodiments described are only for purposes of illustrating the present invention and should not be interpreted as limiting the scope of the invention. Other embodiments of the invention, and certain modifications, combinations and improvements of the described embodiments, will occur to those skilled in the art and all such alternate embodiments, combinations, modifications, improvements are within the scope of the present invention.

Figure 2:
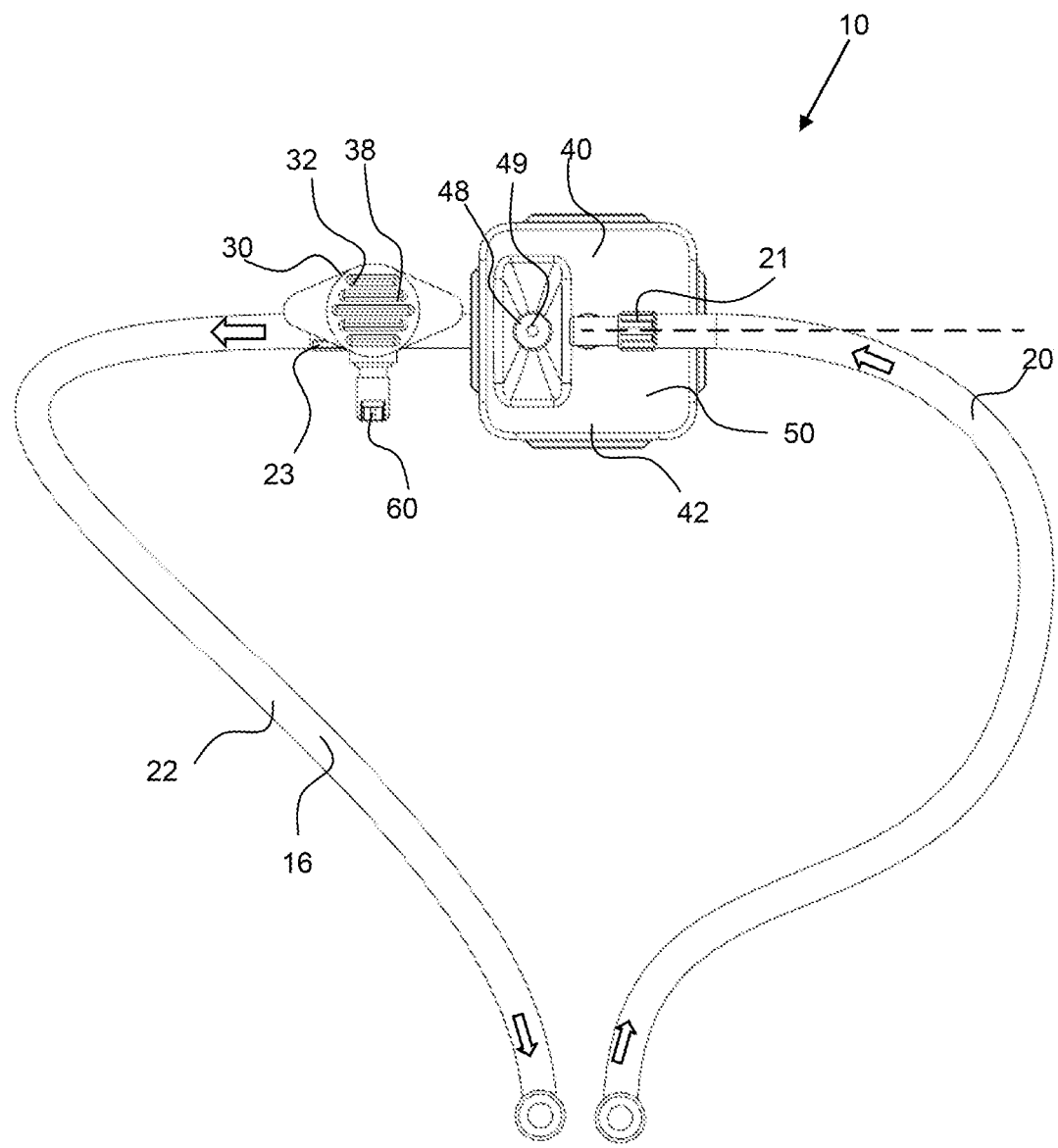
FIG. 2 shows a top view of an exemplary aspiration and filtration system having a filtration unit and a syringe coupled with a flow-valve to control the direction of flow of blood through the system.

Referring to FIGS. 1 and 2, an exemplary aspiration and filtration system 10 is configured to draw bodily fluid 16, such as blood, from a patient 12 through an inlet-sheath 20 and return the flow of bodily fluid to the patient through a return-sheath 22. Blood may be drawn by the syringe 30 into a filter unit 40 where any debris, such as clot particles are collected. The syringe has a syringe barrel 31 that the plunger 32 moves within to draw fluid in and force fluid out. The flow-valve 60 can then be turned to a return direction to direct the filtered blood back into the patient through the return-sheath. An inlet one-way valve 21 is configured between the patient and the filter unit and a return one-way valve 23 is configured between the flow-valve 60 and the patient. The filter unit has a cover 50 that can be removed to inspect and/or remove any debris collect by the filter, therein. This inspection process introduces air into the system, and specifically into the filter housing, that will have to be removed before the flow of bodily fluid in resumed by the system. The flow-valve can be turned to purge direction to direct fluid flow back into the filter unit and force any air through the outlet opening 49 of the purge valve 48. The inlet one-way valve 21 will stop flow back into the inlet sheath 20 and thereby force it out of the purge valve. Note that the outlet opening is above the filter housing to ensure that the trapped air is purged from the filter housing. Also, the purge valve is configured with or coupled to the cover 50 of the filter unit.

Figure 3:
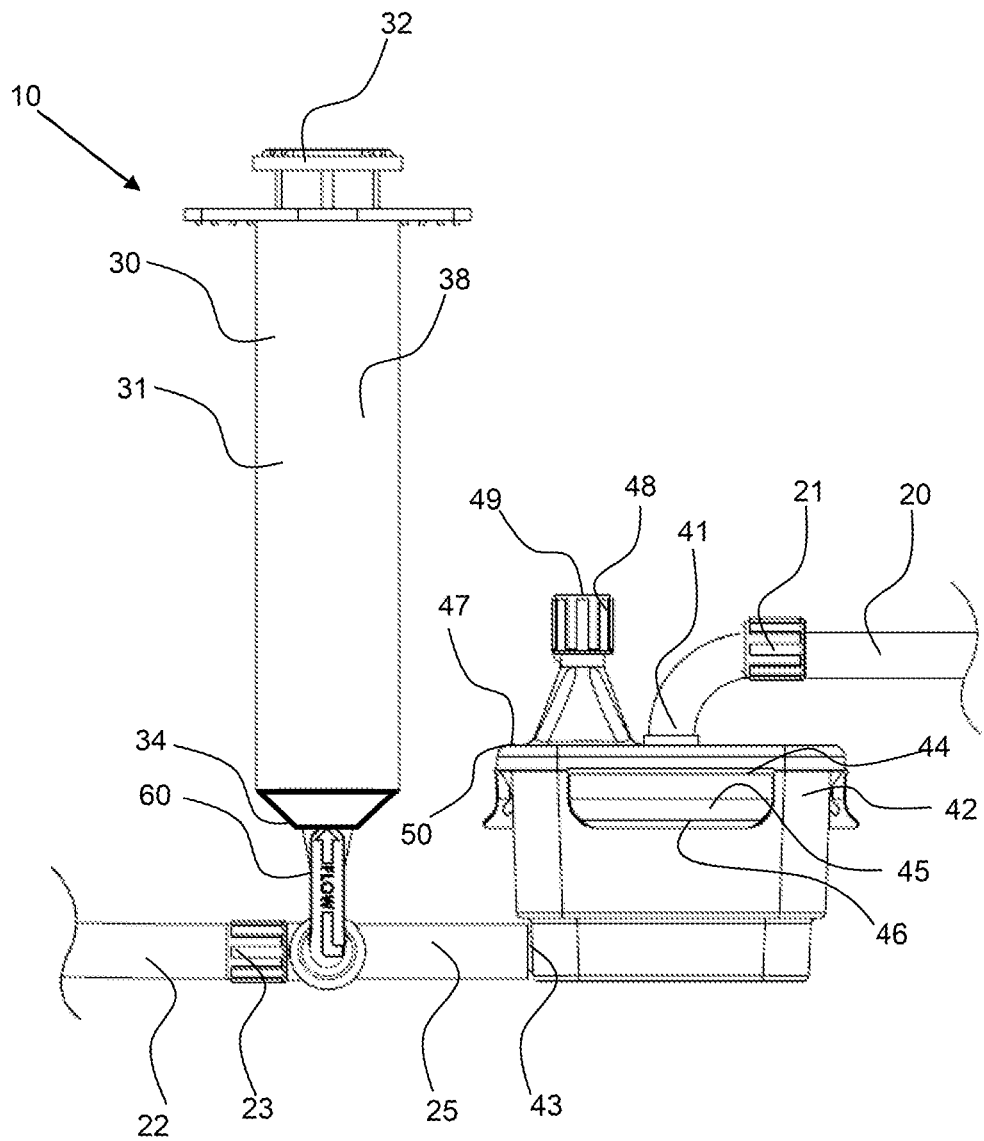
FIG. 3 shows a front view of an exemplary aspiration and filtration system having a filtration unit and a syringe coupled with a flow-valve to control the direction of flow of blood through the system.

As shown in FIG. 3, an exemplary aspiration and filtration system 10 has a filtration unit 40 and a syringe 30 coupled with a flow-valve 60 to control the direction of flow of bodily fluid through the system. The plunger 32 of the syringe can be drawn from the syringe barrel 31 to pull blood into the syringe. Blood flows through the inlet one-way valve 21, through the filter 45 in the filter unit 40, through the filter sheath 25 and into the syringe. The filter sheath, such as a conduit extends from the filter unit 40 and the syringe 30 and may be coupled with the flow valve 60. The flow-valve 60 can then be turned to a return direction to force the fluid from the syringe into the return-sheath. The blood will flow through the flow-valve, through the return one-way valve 23, through the return sheath 22 and back into the patient, or be expelled.

Figure 4:
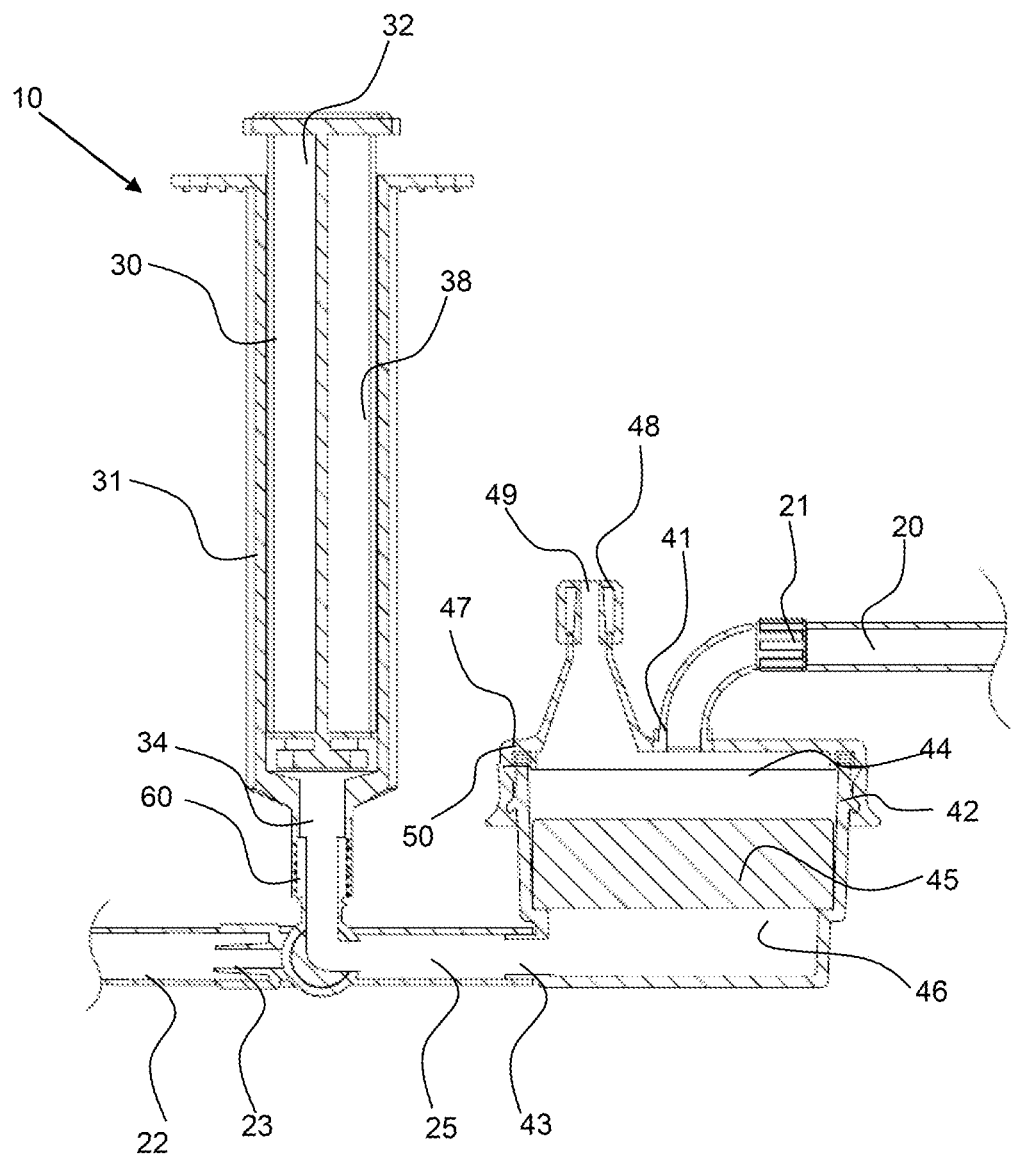
FIG. 4 shows a cross sectional front view of an exemplary aspiration and filtration system having a one-way valve coupled with the inlet-sheath prior to the filtration unit and a purge valve configured on the top of the filtration unit to remove any air after inspection of any debris, such as clot particles, within the filter unit.

As shown in FIG. 4, a filter unit 40 has a filter 45 configured therein to produce a pre-filter portion 44 upstream of the filter, and filtered portion 46 downstream of the filter, when bodily fluid is flowing into the syringe. A cover 50 is configured over the filter housing 42 and a purge valve 48 is configured above the top 47 of the filter unit or filter housing to enable gas, such as air be expelled from the system. The outlet opening 49 of the purge valve is above the enclosed space of the filter unit, or the volume of space within the filter unit from the inlet one-way valve 21 and the outlet 43 of the filter unit or housing. There is a volume for the flow of bodily fluid from the inlet one-way valve to the inlet 41 of the filter unit, or housing. It may be desirable for the inlet one-way valve to be configure proximal to the filter housing or be configured between the filter housing and the inlet sheath. The inlet one-way valve may be coupled to and between the filter housing and the inlet sheath, for example.

Figure 5:
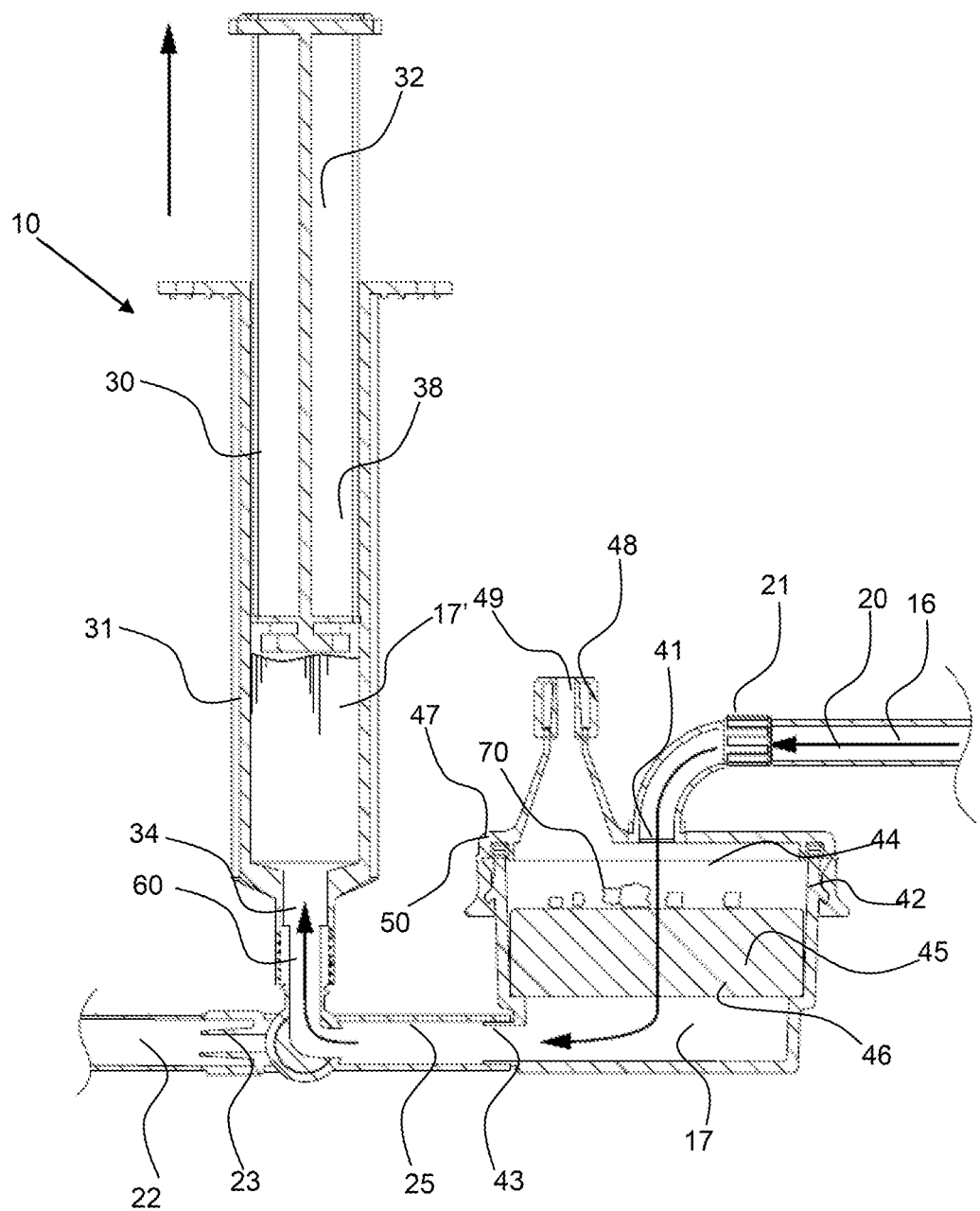
FIG. 5 shows a cross sectional view of the exemplary aspiration and filtration system shown in FIG. 4, drawing blood into the filter unit by the syringe, wherein the plunger of the syringe is being pulled out of the syringe to create suction; debris is being collected on the filter.

As shown in FIG. 5, the exemplary aspiration and filtration system shown in FIG. 4, is drawing bodily fluid 16, such as blood, into the filter unit 40 by the syringe 30, wherein the plunger 32 of the syringe is being pulled out of the syringe barrel 31 to create suction. Debris 70, such as clot debris and plaque, is being collected on the filter 45. The filtered fluid 17, 17' is drawn into the syringe. The flow-valve 60 is configured in a filter direction to allow inlet flow of bodily fluid into the filter unit 40 in this process step of the aspiration and filtration method.

Figure 6:
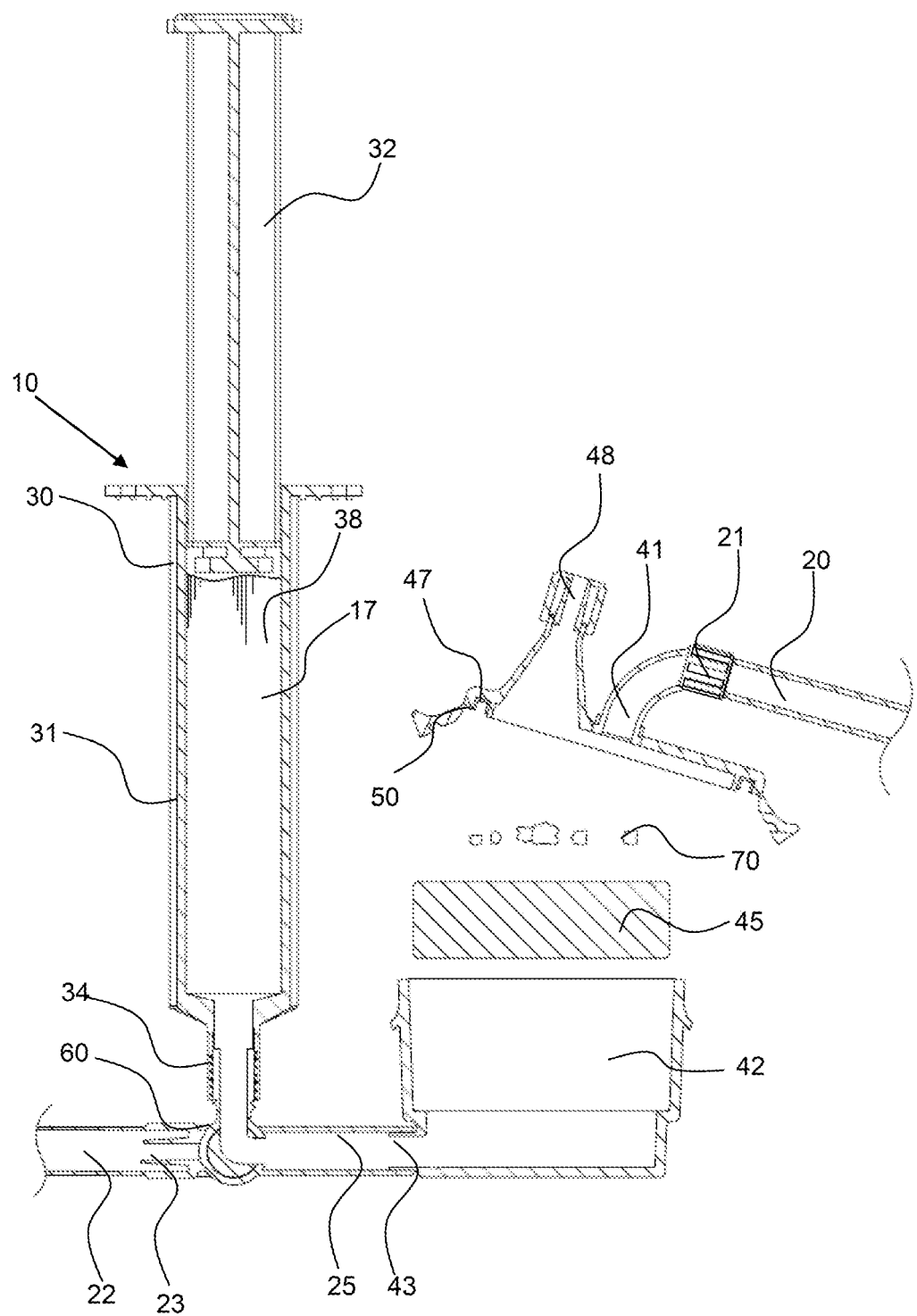
FIG. 6 shows a cross sectional view of the exemplary aspiration and filtration system shown in FIG. 5, having the filter unit cover removed to enable inspection and removal of the debris.

As shown in FIG. 6, the exemplary aspiration and filtration system shown in FIG. 5 has the filter unit cover 50 removed to enable inspection and removal of the debris 70. As described herein, this will introduce air into the system.

Figure 7:
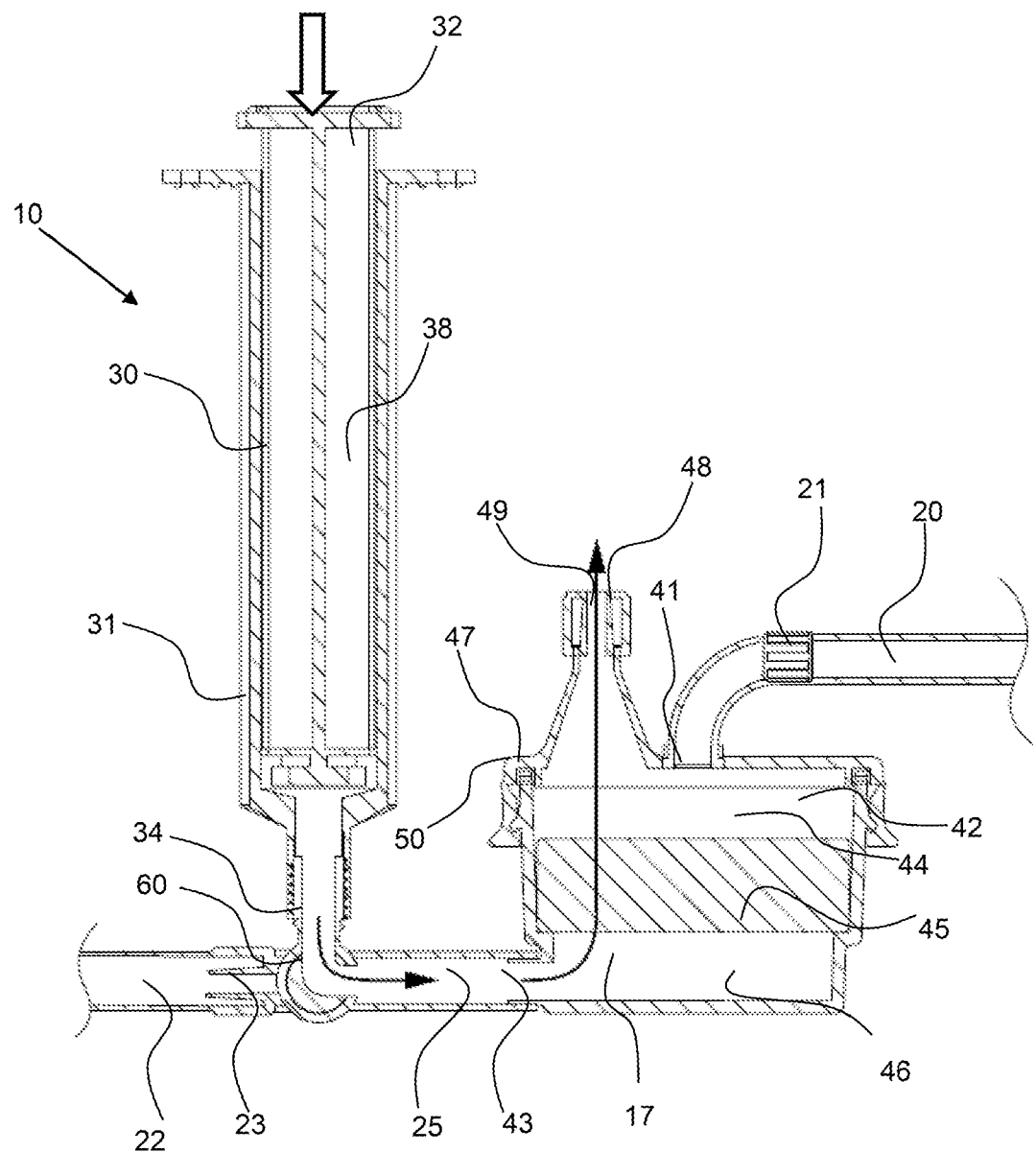
FIG. 7 shows a cross sectional view of the exemplary aspiration and filtration system shown in FIG. 6, having the filter unit cover replaced and the flow-valve turned to or configured in a purge direction to force blood from the syringe back into the filter unit to remove any gas, such as air through the purge valve configured above the filter housing.

As shown in FIG. 7, the exemplary aspiration and filtration system 10 shown in FIG. 6 has the filter unit cover 50 replaced and the flow-valve 60 is still in the filter direction, or a purge direction now as pushing the plunger 32 back into the syringe barrel 31 causes the filtered fluid 17 to flow from the syringe back into the filter unit 40 to purge trapped air from the filer housing 42. Gas in the filter unit will flow through the outlet opening 49 of the purge valve 48 as the plunger is depressed. Note that the inlet one-way valve 21 prevents flow of fluid back into the inlet-sheath.

Figure 8:
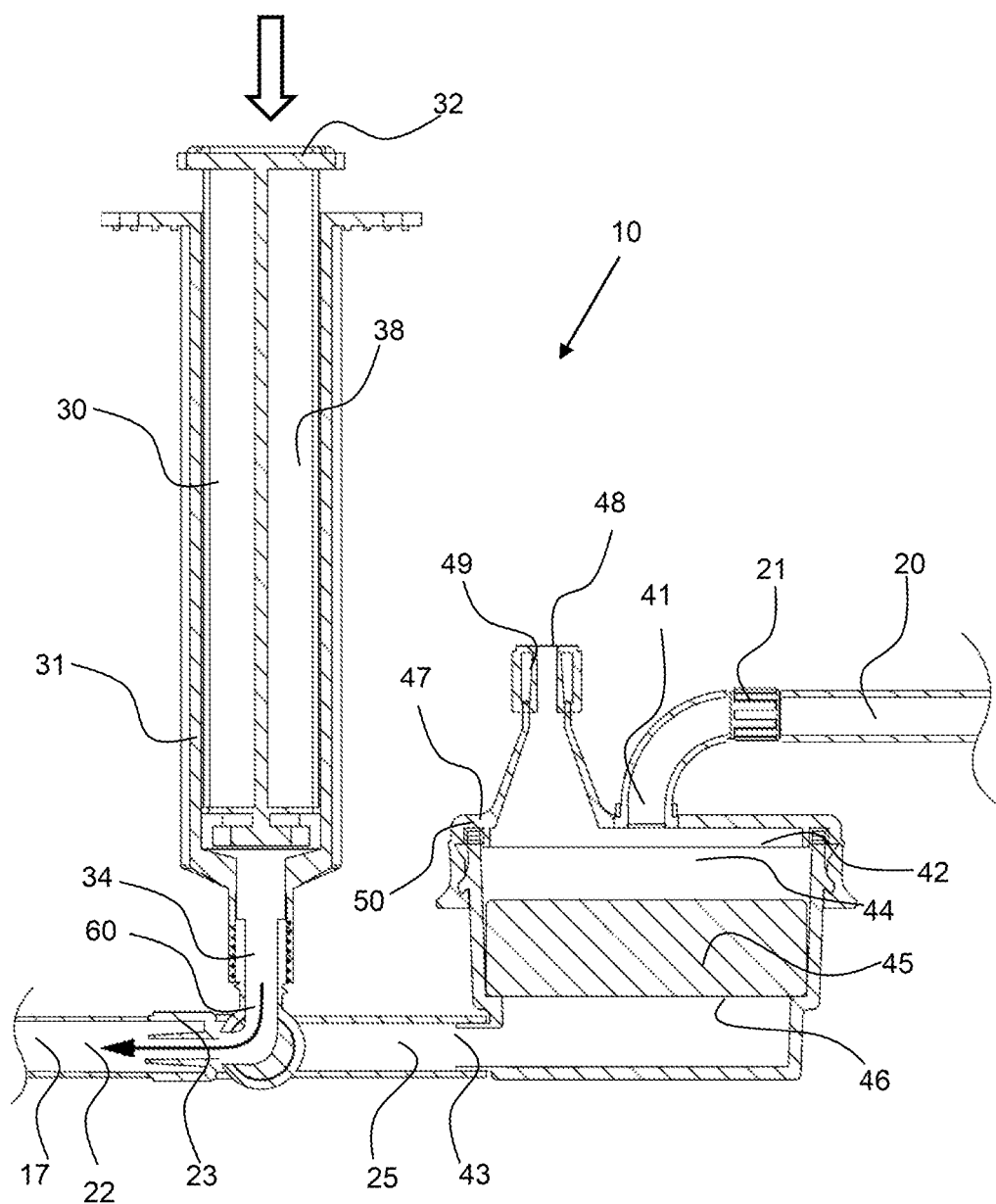
FIG. 8 shows a front cross sectional view of an exemplary aspiration and filtration system having the flow-valve turned in a return direction to return filtered blood back to the patient.

As shown in FIG. 8, an exemplary aspiration and filtration system 10 has the flow-valve 60 turned in a return direction to return filtered fluid 17 back to the patient through the return one-way valve 23 and the return-sheath 22.

Figure 9:
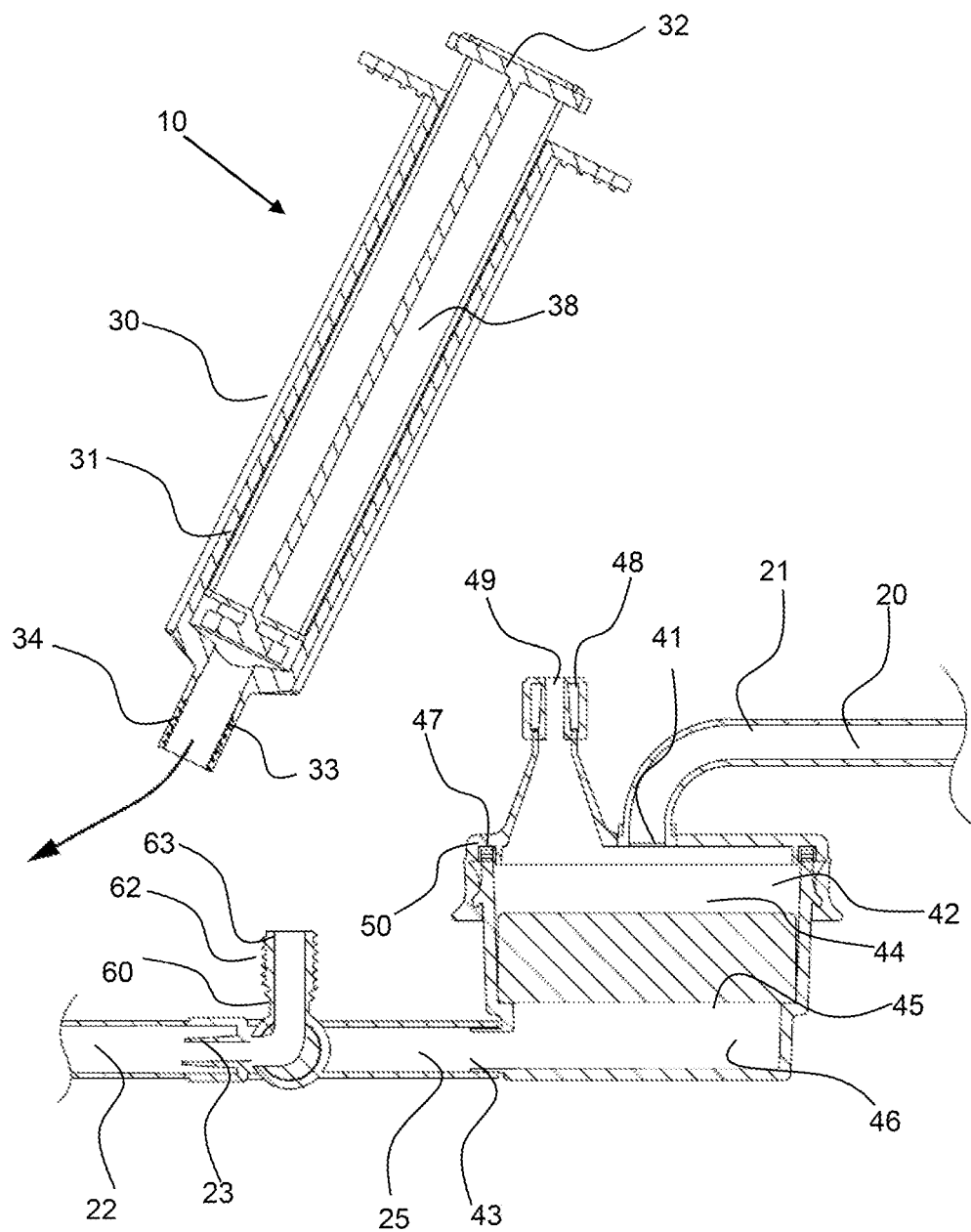
FIG. 9 shows a front cross sectional view of an exemplary aspiration and filtration system with the syringe removed from the flow-valve.

As shown in FIG. 9 an exemplary aspiration and filtration system 10 has the syringe 30 removed from the flow-valve 60. The syringe has a coupled end 34, or end that couples with the flow-valve, such as through a luer lock, an example of a valve syringe coupling 62. A Luer lock has threads 63 that couple with the threads 33 of the coupled end 34 of the syringe.

Figure 10:
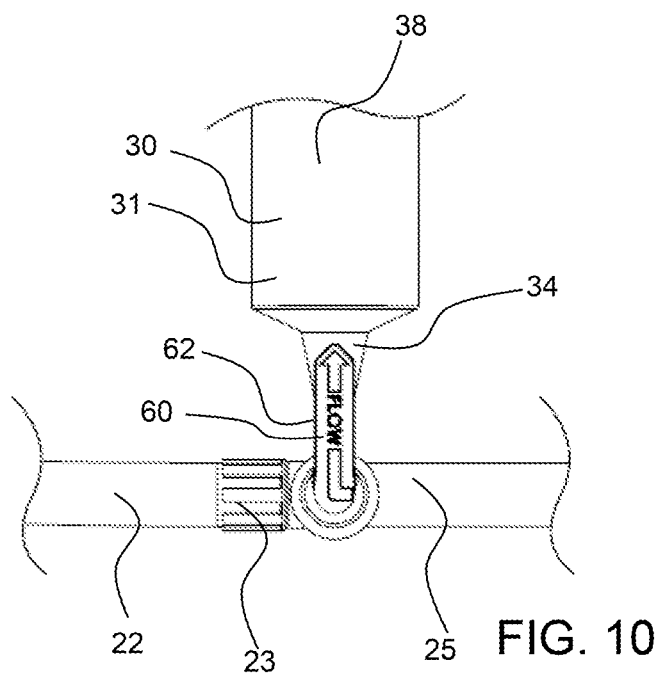
FIG. 10 shows a front view of an exemplary flow-valve coupled with a return-sheath and the flow-valve turned in a filter direction for producing an inlet flow of blood into the filter unit.

As shown in FIG. 10, an exemplary flow-valve 60 is coupled with a return-sheath 22 and the flow-valve is configured in an inlet flow configuration, or filter direction, to allow a flow of filtered fluid into the syringe or a flow of filtered fluid back into the filter unit to purge any air.

Figure 11:
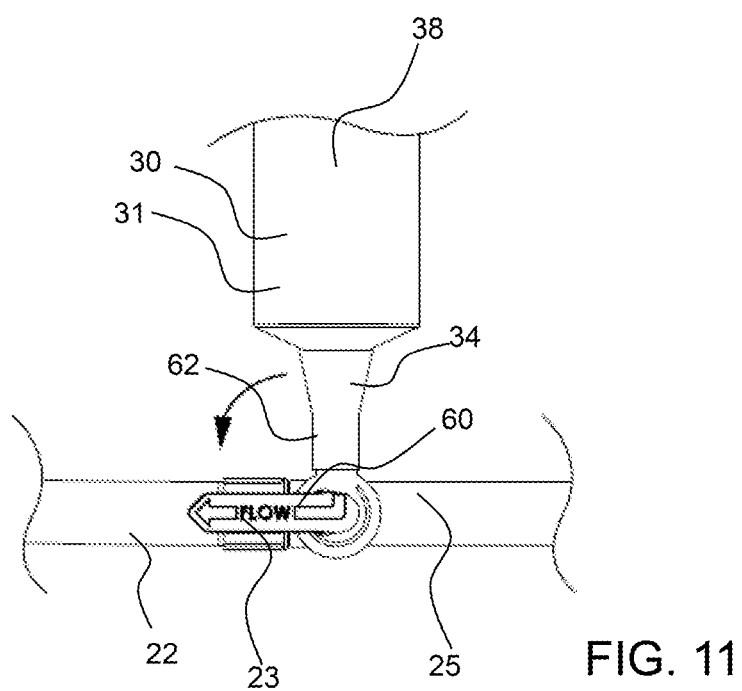
FIG. 11 shows a front view of an exemplary flow-valve coupled with a return-sheath and the flow-valve turned in a return direction for directing a flow of blood to the patient.

As shown in FIG. 11, an exemplary flow-valve 60 is coupled with a return-sheath 22 and the flow-valve 60 is configured in a return flow configuration, or return direction, to force fluid from the syringe through the return sheath 22 to the patient or to expel the fluid.

Figure 12:
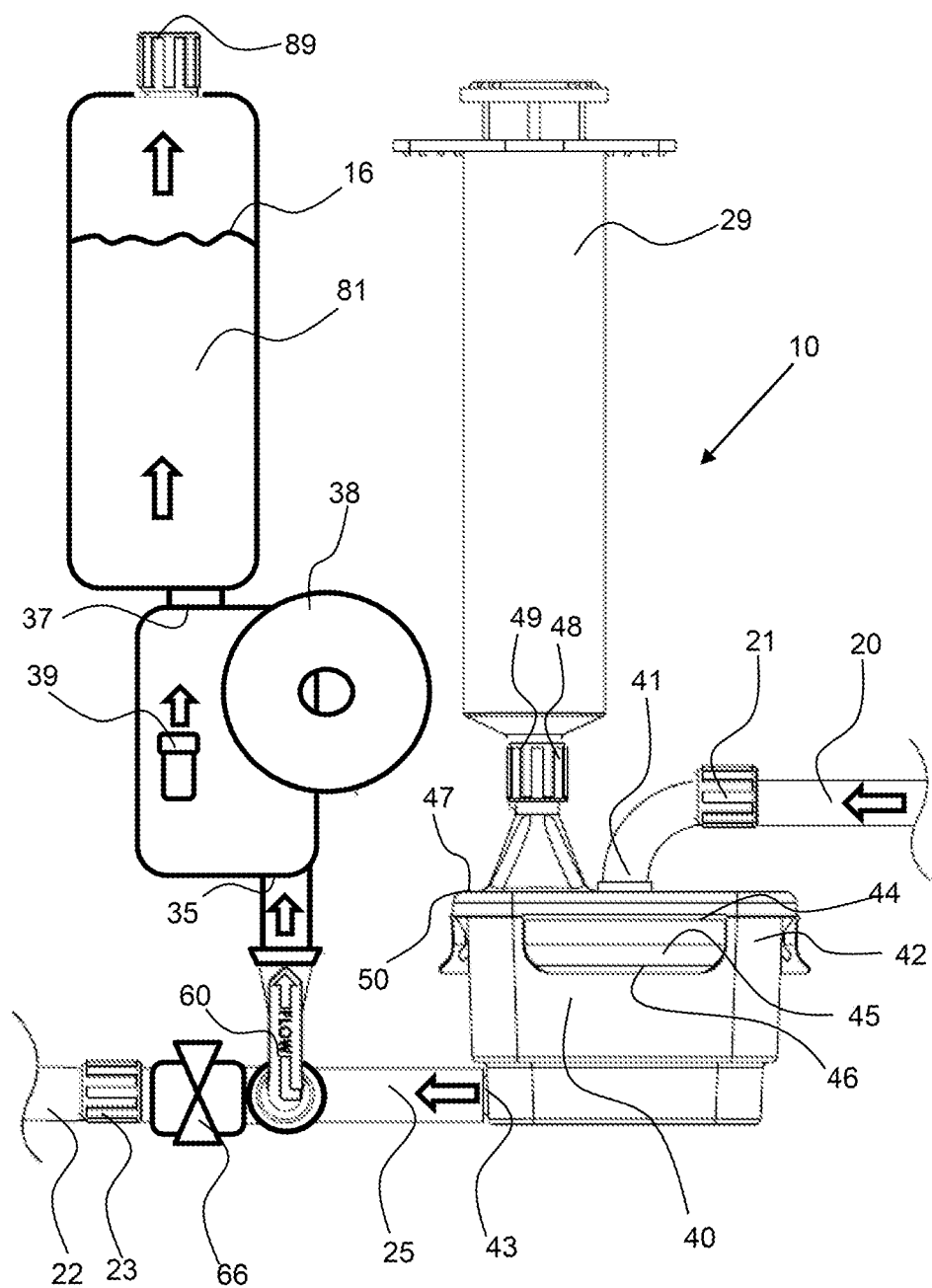
FIG. 12 shows a front view of an exemplary aspiration and filtration system having a pump coupled with a reservoir and having a direction switch to control the direction of fluid pumped by the pump; bodily fluid is being pumped into the reservoir by the pump.
Figure 13:
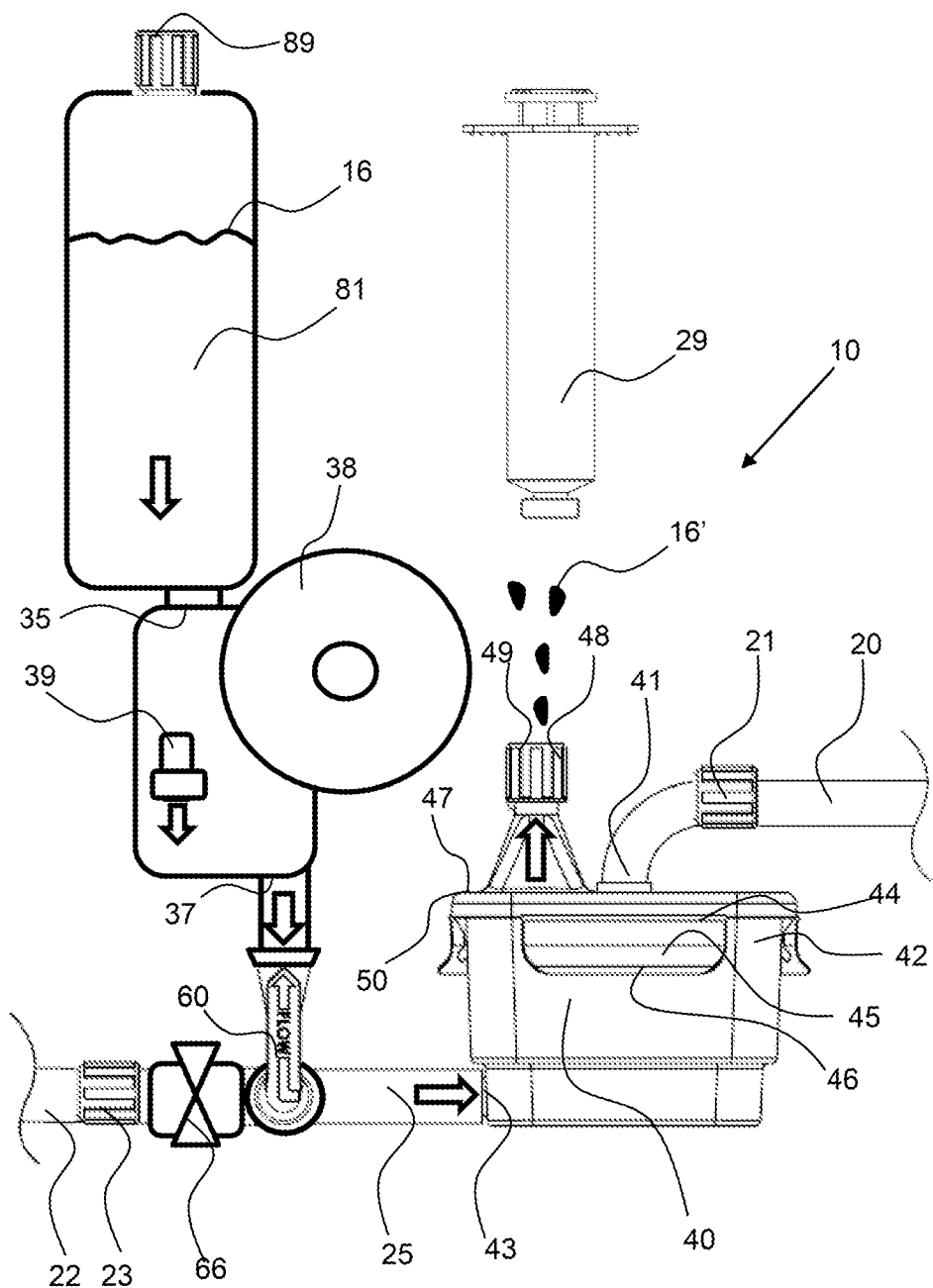
FIG. 13 shows a front view of the aspiration and filtration system shown in FIG. 12, with the direction switch reversed from FIG. 12 and the bodily fluid being pumped back into the filter unit to purge air from the filter unit through the purge valve 48.
Figure 14:
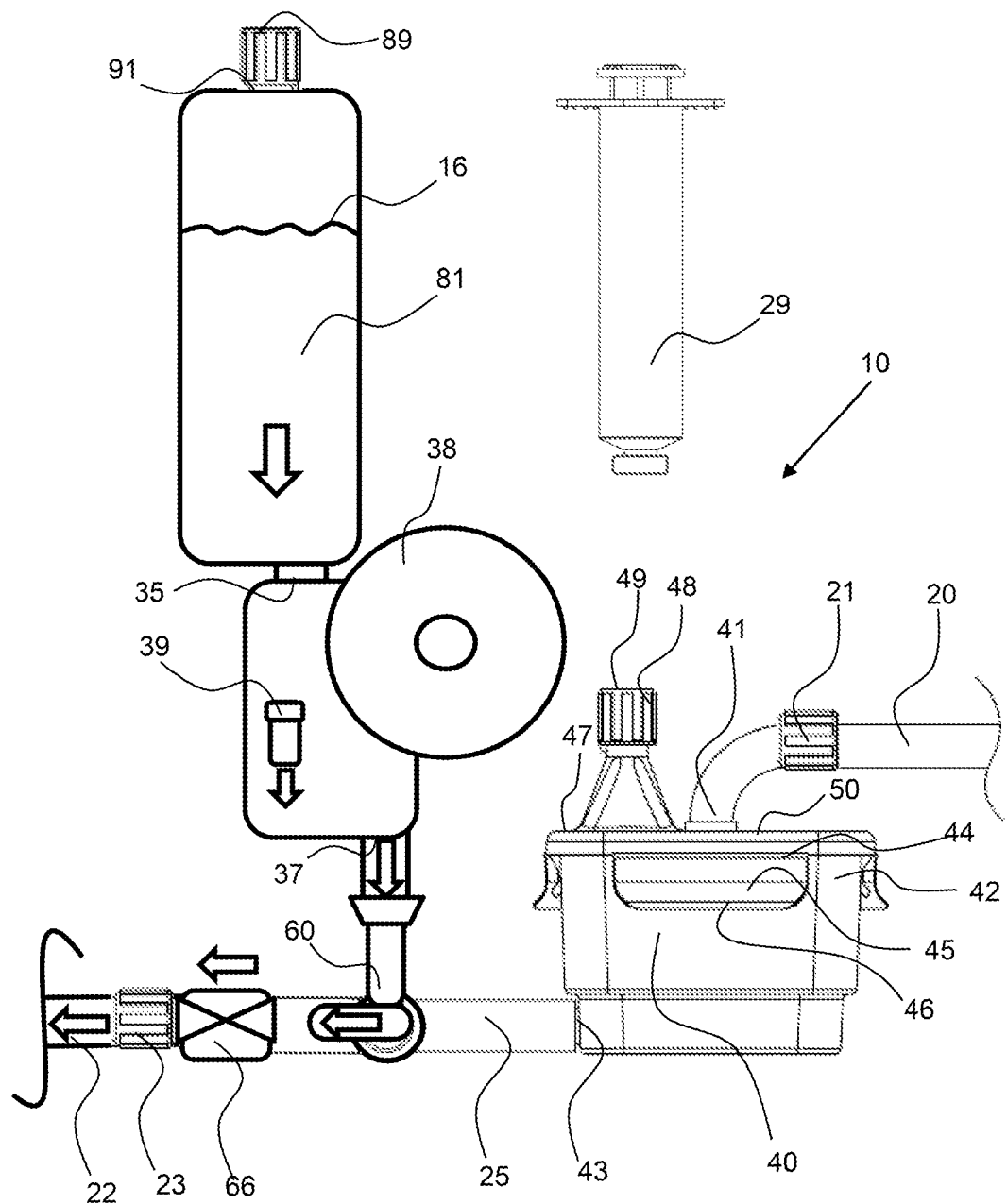
FIG. 14 shows a front view of the aspiration and filtration system shown in FIG. 12, with the direction switch reversed and also the flow-valve switch to force the bodily fluid into the return sheath, which may be coupled with the patient.

Referring now to FIGS. 12 to 14, an exemplary aspiration and filtration system 10 has a pump 38 configured between the filter unit 40 and the return sheath 22. A reservoir 81 for the bodily fluid is coupled with the pump 38 to collect a volume of bodily fluid. As shown in FIG. 12, the direction switch 39 is configured to pump the bodily fluid 16 through the pump inlet 35 through the pump outlet 37 and into the reservoir 81. A reservoir purge valve 89 allows air to be purged from the reservoir as bodily fluid 16 is pumped therein. An additional reservoir may be coupled to the reservoir opening 91 coupled with the reservoir purge valve 89. The reservoir may also be a collapsible reservoir, such as a bag. A volume of bodily fluid, such as blood, is pumped through the filter unit 40 and the filter 45 therein and subsequently into the reservoir 81. As shown in FIG. 13, the directional switch 39 is reversed from the direction shown in FIG. 12 and now the bodily fluid 16 within the reservoir is pumped through the inlet 35 of the pump 38, through the outlet of the pump 37, through the flow valve 60 and back into the filter unit 40. When all the air is purged, bodily fluid 16' may be expelled through the purge valve. Note that the inlet and the outlet of the pump changed as a function of the directional switch.

A return valve 66 may be configured between the flow-valve 60 and the return sheath 22 and may be configured between the return one-way valve 23 and the flow valve. The return valve 66 may be configured to allow flow into the return sheath or to stop flow to the return sheath. This valve may be turned to stop flow as a back-up valve and flow stop when the bodily fluid is pumped back into the filter unit to expel and purge air from the filter unit. Also, a syringe 29 may be coupled with the purge valve 48 configured on the cover 50 of the filter unit 40 to draw air out from the filter unit after the cover has been replaced. This is an optional way to purge air from the filter unit and system prior to resuming filtration of bodily fluid through the filter in the filter unit.

As shown in FIG. 14, the directional switch 39 is set to a return direction, wherein the bodily fluid 16 is pumped from the reservoir 81 through the flow-valve and into the return sheath 22. The cycle from FIG. 12 to FIG. 14 may be repeated a number of times before the filter unit is opened to inspect and or replace the filter. The cycle shown in FIG. 13 may then be used to purge the filter unit of air before drawing more bodily fluid through the filter.

Figure 15:
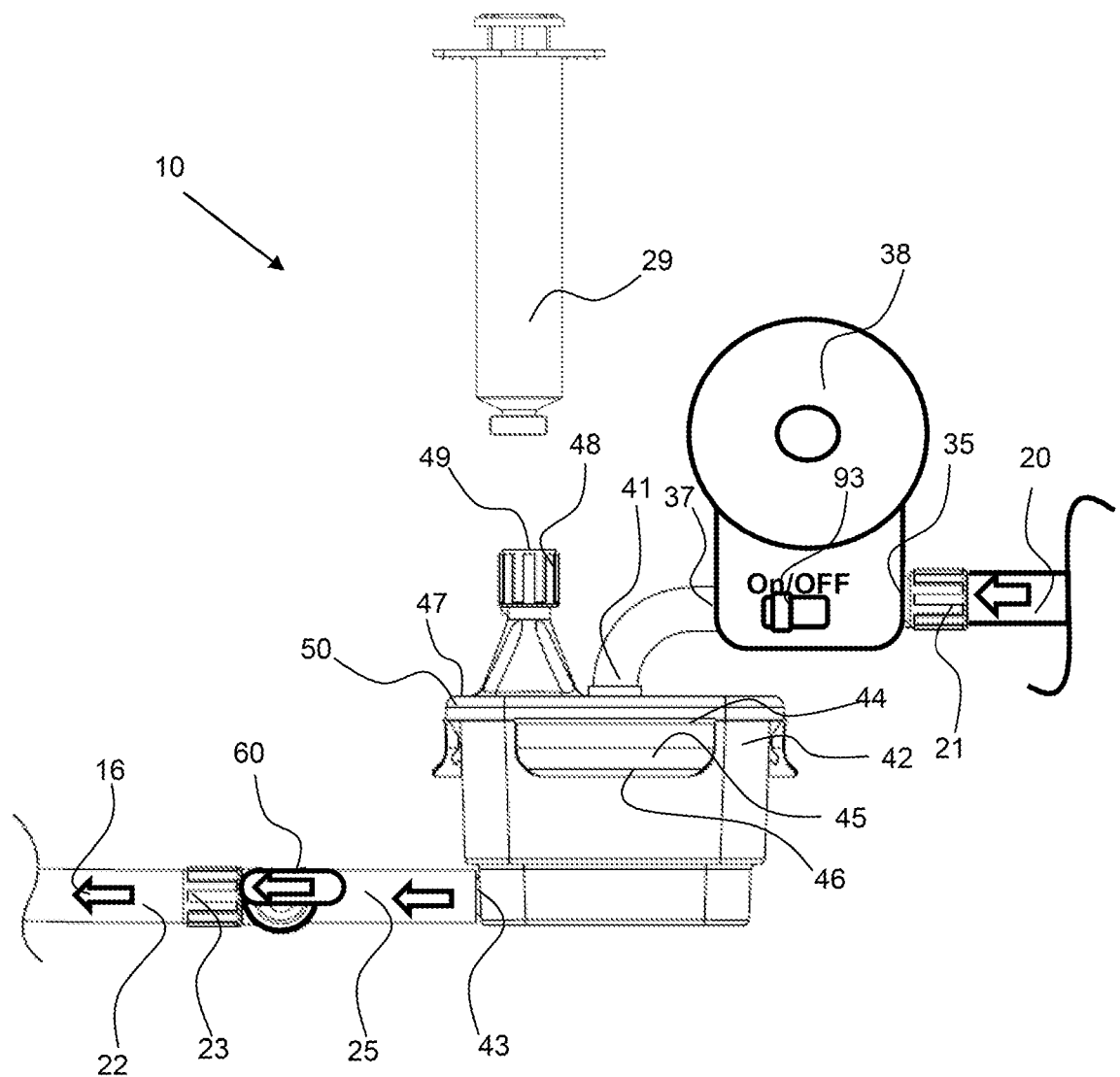
FIG. 15 shows a front view of an exemplary aspiration and filtration system having a pump configured between the inlet sheath and the filter unit with the flow-valve configured to pump bodily fluid through the filter unit and then through the return sheath.
Figure 16:
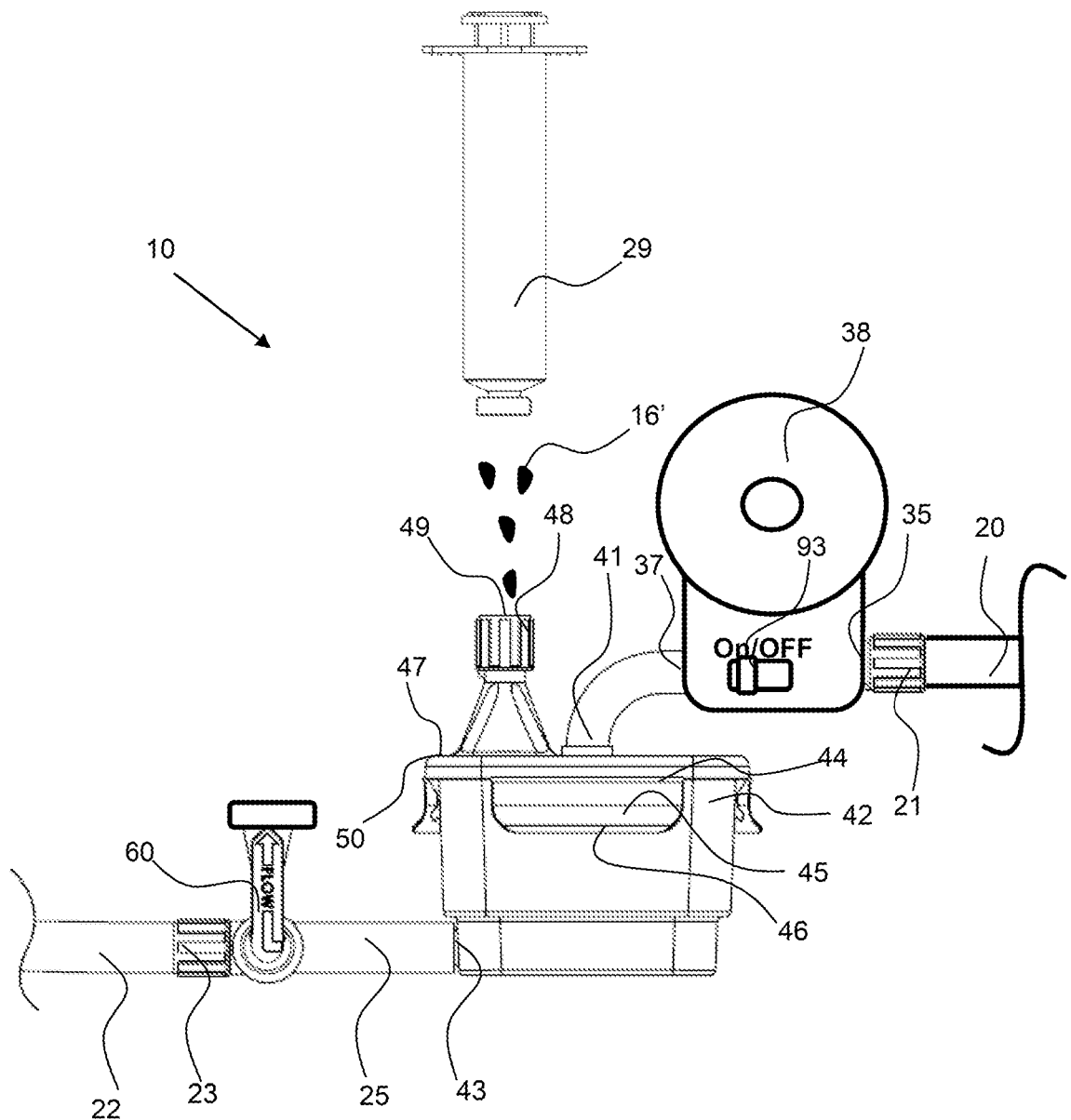
FIG. 16 shows a front view of the exemplary aspiration and filtration system shown in FIG. 15, with the flow-valve now in a flow-stop configuration to allow bodily fluid to be pumped into the filter until to purge air from the filter unit before filtration of the bodily fluid is resumed.

Referring now to FIGS. 15 and 16, an exemplary aspiration and filtration system 10 has a pump 38 configured between the inlet sheath 20 and the filter unit 40. The pump has an on/off switch 93 that is used to control the flow of bodily fluid into the filter unit 40. As shown in FIG. 15, the pump is on and the flow-valve is set to direct the bodily fluid 16 to the return sheath 22 after it has been pumped through the filter 40 unit and filter 45. As shown in FIG. 16, the flow-valve 60 is turned to a flow-stop configuration, wherein air in the filter unit 40 is purged through the purge valve 48 in the cover 50 of the filter unit. Also, a syringe 29 may be coupled with the purge valve 48 configured on the cover 50 of the filter unit 40 to draw air out from the filter unit after the cover has been replaced. This is an optional way to purge air from the filter unit and system prior to resuming filtration of bodily fluid through the filter in the filter unit.

It will be apparent to those skilled in the art that various modifications, combinations and variations can be made in the present invention without departing from the scope of the invention. Specific embodiments, features and elements described herein may be modified, and/or combined in any suitable manner. Thus, it is intended that the present invention cover the modifications, combinations and variations of this invention provided they come within the scope of the appended claims and their equivalents.

What is claimed is:

1. An aspiration and filtration system for bodily fluid comprising:
   a) an inlet-sheath;
   b) an inlet one-way valve coupled to the inlet-sheath;
   c) a return-sheath;
   d) a filter unit comprising:
      i) a filter housing having an inlet and an outlet;
      ii) a filter configured in the filter housing between the inlet and the outlet;
      iii) a cover that is detachably attachable to the filter housing and configured over a top of the filter housing;
   wherein the filter unit is configured to receive said bodily fluid into the inlet from a patient and wherein said bodily fluid is configured to flow through the filter to the outlet of the filter unit, wherein the filter filters particles from the bodily fluid between the inlet and the outlet within the filter housing;
      wherein the filter is separate from the filter housing and the cover;
      wherein the filter is removable from the filter housing by removing the cover;
   e) a purge valve coupled to the filter cover and having an outlet opening configured above the filter housing to enable purging trapped air from the filter unit with said bodily fluid contained within the filter unit;
   f) a pump configured to force said bodily fluid into the filter unit;
   g) a flow-valve coupled with the pump;
      wherein the flow-valve is configured for turning from an inlet flow configuration to a purge flow configuration;
      wherein the flow-valve has said inlet flow configuration for drawing said bodily fluid through the inlet-sheath, through the filter housing and into a syringe, whereby debris from the bodily fluid is collected by the filter;

wherein the flow-valve has said purge flow configuration for forcing said bodily fluid from the syringe into the filter unit and the air out of the outlet opening of the purge valve; and wherein the flow-valve has a return flow configuration for forcing said bodily fluid from the syringe into the return-sheath; wherein the return-sheath is a separate sheath from the inlet-sheath, and wherein the return-sheath is configured between the outlet of the filter housing and said patient; and wherein the cover of the filter unit is configured to be removed from said top of the filter housing for inspection and removal of said particles, and wherein said filter within the filter housing is configured to be removed from the filter housing and replaced with a new filter.

2. The aspiration and filtration system of claim 1, wherein the pump is a powered pump configured between the filter unit and the return sheath.

3. The aspiration and filtration system of claim 2, further comprising a reservoir coupled to the pump to receive said bodily fluid from the filter unit.

4. The aspiration and filtration system of claim 1, wherein the pump comprises a directional switch to control a direction of pumping, wherein the pump is configured to pump said bodily fluid into a reservoir or from the reservoir.

5. The aspiration and filtration system of claim 4, wherein the reservoir has a reservoir purge valve.

6. The aspiration and filtration system of claim 5, wherein the filter housing has a volume that is less than a volume of the reservoir.

7. The aspiration and filtration system of claim 1, wherein the pump is configured between the flow valve and a reservoir.

8. The aspiration and filtration system of claim 1, wherein the pump is configured between the inlet sheath and the filter unit.

9. The aspiration and filtration system of claim 8, wherein the pump has a on/off switch.

10. The aspiration and filtration system of claim 1, wherein the bodily fluid is blood and the debris comprises thrombus.

11. A method of aspiration and filtration of particles from blood comprising:

a) providing the aspiration and filtration system of claim 1;
b) coupling the inlet-sheath to an artery of the patient;
c) setting the flow-valve to the inlet flow configuration;
d) pumping said blood from the artery, through the inlet-sheath, through the inlet one-way valve, into the filter housing;
e) filtering the particles on the filter and producing a volume of filtered blood;
f) stopping the pump and removing the filter cover;
g) replacing the filter cover on the filter unit;
h) setting the flow-valve to prevent said blood from flowing into the return sheath;
i) turning on the pump to pump said blood into the filter housing to purge said air from the filter unit;
j) again, setting the flow-valve to the inlet flow configuration; and
k) pumping said blood to the return sheath.

12. The method of claim 11, wherein the pump is a powered pump configured between the filter unit and the return sheath.

13. The method of claim 12, further comprising a reservoir coupled to the pump to receive said blood from the filter unit.

14. The method of claim 13, wherein the pump comprises a directional switch to control a direction of pumping, wherein the pump is configured to pump said blood into the reservoir or from the reservoir.

15. The method of claim 14, wherein the reservoir has a reservoir purge valve.

16. The method of claim 15, wherein the filter housing has a volume that is less than a volume of the reservoir.

17. The method of claim 16, wherein the blood is pumped into the reservoir and after the filter cover is removed, said blood within the reservoir is pumped back into the filter housing when the pump is used to pump said blood into the filter housing to purge said air from the filter unit.

18. The method of claim 17, wherein the pump is configured between the flow valve and the reservoir.

19. The method of claim 11, wherein the pump is configured between the inlet sheath and the filter unit.

20. The method of claim 19, wherein the pump has an on/off switch.

* * * * *